United States Patent [19]
Cobbs et al.

[11] Patent Number: 5,916,746
[45] Date of Patent: Jun. 29, 1999

[54] FORMAZAN-BASED IMMUNOASSAY

[75] Inventors: Carrington S. Cobbs, Ellicott City; Thomas M. Woerner, Westminster, both of Md.

[73] Assignee: Kirkegaard & Perry Laboratories, Inc., Gaithersburg, Md.

[21] Appl. No.: 08/647,314

[22] Filed: May 9, 1996

[51] Int. Cl.$^6$ .............................. C12Q 1/68; G01N 33/53
[52] U.S. Cl. .............................. 435/6; 435/7.9; 435/7.92; 435/7.93; 435/7.94; 435/7.95; 435/21; 435/962; 435/963; 435/975; 436/518; 436/524; 436/527; 436/528; 436/529; 436/530; 436/531; 436/808
[58] Field of Search .................................. 435/6, 7.1, 7.9, 435/7.92–7.95, 21, 962, 963, 975; 436/518, 524, 527, 528–531, 808

[56] References Cited

U.S. PATENT DOCUMENTS

| | | |
|---|---|---|
| 4,012,286 | 3/1977 | Sanderson et al. . |
| 4,024,021 | 5/1977 | Stavropoulos et al. . |
| 4,215,197 | 7/1980 | Tarbutton . |
| 4,247,633 | 1/1981 | Case et al. ................................. 435/17 |
| 4,254,222 | 3/1981 | Owen ........................................ 435/26 |
| 4,309,502 | 1/1982 | Lauderdale ................................ 435/15 |
| 4,351,899 | 9/1982 | Owen ........................................ 435/26 |
| 4,613,569 | 9/1986 | Geisler et al. ............................ 435/26 |
| 4,642,295 | 2/1987 | Baker ....................................... 436/87 |
| 4,645,742 | 2/1987 | Baker ....................................... 436/15 |
| 4,847,194 | 7/1989 | Quante ..................................... 435/7.9 |
| 4,847,196 | 7/1989 | Geisler et al. ............................ 435/26 |
| 4,849,347 | 7/1989 | Familletti et al. ........................ 435/34 |
| 4,892,816 | 1/1990 | Akiba et al. .............................. 435/11 |
| 4,892,817 | 1/1990 | Pawlak ..................................... 435/21 |
| 4,898,813 | 2/1990 | Albarella et al. .......................... 435/4 |
| 4,940,660 | 7/1990 | Hirai et al. ............................... 435/7.9 |
| 4,956,301 | 9/1990 | Ismail et al. .............................. 436/87 |
| 5,122,454 | 6/1992 | Ueda et al. ............................... 435/15 |
| 5,139,934 | 8/1992 | Stewart et al. .......................... 435/7.92 |
| 5,156,947 | 10/1992 | Siedel et al. ............................. 435/4 |
| 5,294,540 | 3/1994 | Daniel et al. ............................. 435/25 |
| 5,354,658 | 10/1994 | Wright ....................................... 435/6 |

FOREIGN PATENT DOCUMENTS 1351547  3/1972  United Kingdom .

OTHER PUBLICATIONS

International Search Report of PCT/US97/07658 dated Aug. 14, 1997.
Heegaard, N.H.H. "Visualization of alkaline phosphatase–labelled antibodies on immunoblots by means of formazan staining using indoxyl phosphate and thiazolyl blue," Applied and Theoretical Electrophoresis 1(5):261–264, 1990.
Altman, "Tetrazolium Salts and Formazans", *Progr. Histochem. Cytochem.* 9(*3*):1–56 (1976).
Altman, "Studies on the Reduction of Tetrazolium Salts . . . ", *Histochemistry* 38:155–171 (1974).
Blake et al., "A Rapid, Sensitive Method for Detection of Alkaline Phosphatase–Conjugated Anti–Antibody on Western Blots", *Analytical Biochemistry* 136:175–170 (1984).
Kugler, "Quantitative Dehydrogenase Histochemistry with Exogenous Electron Carriers", *Histochemistry* 75:99–112 (1982).
Heegaard, "Visualization of Alkaline . . . ", *Applied and Theoretical Electrophoresis* 1:261–264 (1990).
D.J. Colgan, "Spectrophotometric quantitation of DIVA on blots after ethanol–solubilization of the MTT–formazan . . . ", Applied and Theoretical Electroph. 3:219–222 (1993).
A Cory et al., "Use of an Aqueous Soluble Tetrazolium/Formazan Assay for Cell Growth Assays in Culture," Cancer Commun. 3(7):202–212 (1991).
M. Ishiyama et al., "Novel Cell Proliferation and Cytotoxicity Assays Using . . . a Water–Soluble Formazan Dye," In vitro Toxicology 8(2):187–190 (Summer 1995).

*Primary Examiner*—Carol A. Spiegel
*Attorney, Agent, or Firm*—Banner & Witcoff, Ltd.

[57] ABSTRACT

This invention relates to an improved method for detecting and quantifying the presence of a target molecule, such as an antigen, an antibody or a polynucleotide, in a sample which method uses alkaline phosphatase as the reporter enzyme and the reduction of a tetrazolium salt to a formazan as part of the detection/signaling system.

28 Claims, 1 Drawing Sheet

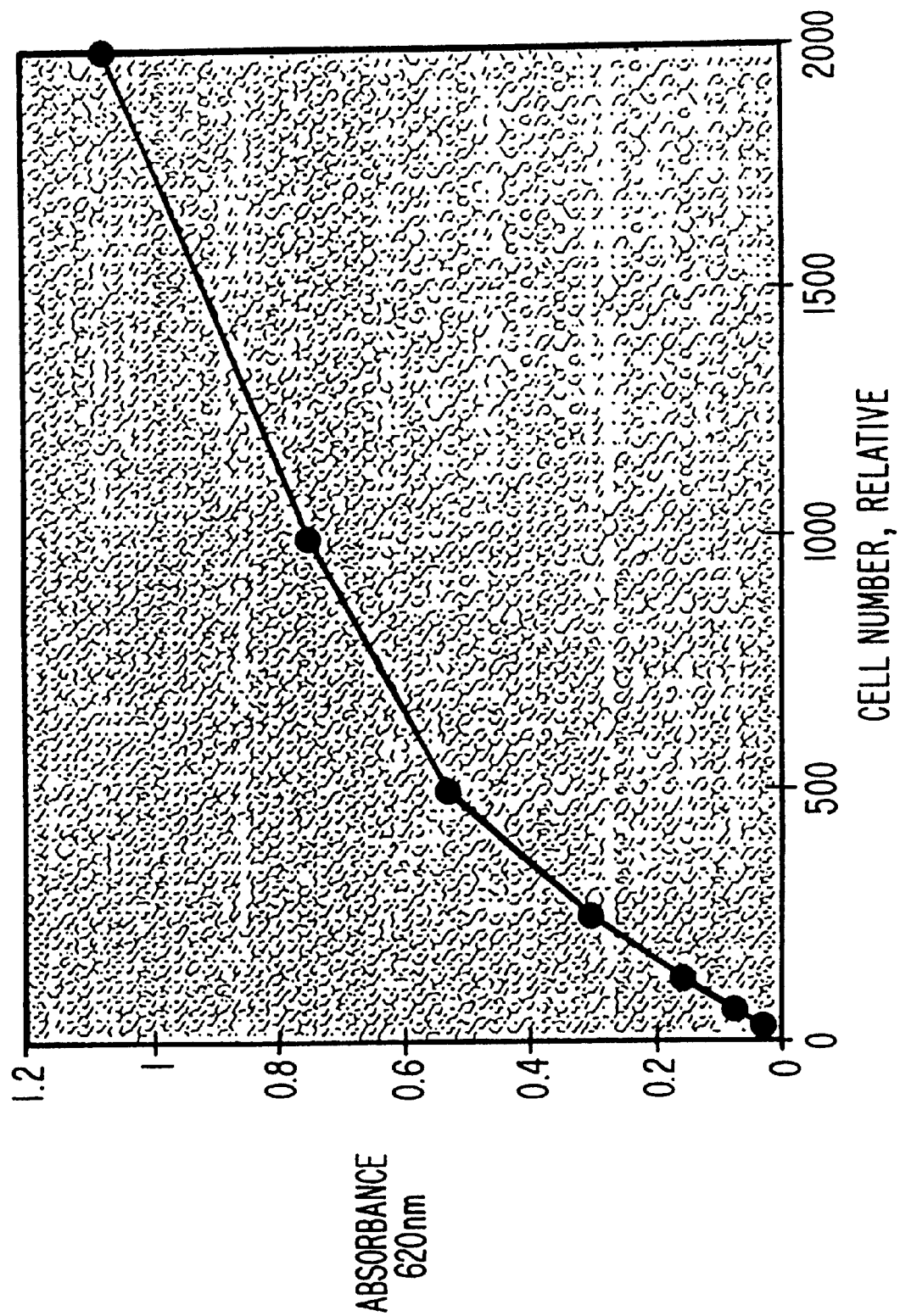

FORMAZAN-BASED IMMUNOASSAY

BACKGROUND OF THE INVENTION

1. Field of the Invention

This invention broadly relates to an improvement in methods for detecting and especially for quantifying the presence of a target molecule, such as an antigen, an antibody or a polynucleotide, in a sample. More particularly, the invention relates to an improved method for conducting an immunoassay or a polynucleotide hybridization assay, which method uses alkaline phosphatase as the reporter enzyme and a reduction of a tetrazolium salt to a formazan as the detection/signaling system for detecting or quantifying a target molecule such as may be present in a biological sample.

2. Description of Related Art

The analysis and detection of minute quantities of substances in biological and non-biological samples, both qualitative and quantitative, has become a routine practice in clinical, diagnostic and analytical laboratories. The most prevalent detection techniques are based on ligand-receptor interactions (e.g., immunoassay-based techniques) and polynucleotide hybridizations.

Immunoassay-based techniques are characterized by a sequence of steps comprising the non-covalent binding of an antibody with an antigen complementary to it. Such assays have been used to detect antibodies produced in response to infection, components of pathological agents, levels of drugs, hormones, enzymes, etc. In addition to medicinal applications, immunoassays also have been applied in the manufacturing industries, for example, for the detection of food contaminants.

In one approach, commonly referred to as a sandwich assay, a sample to be tested for the presence of a particular target molecule which is one member of an immunological complementary binding pair, is bound to a surface of a solid support. The surface can either be nonimmunological or can harbor an excess of the complement of the desired target molecule (i.e., corresponding antibody or antigen). The surface containing the bound sample then is exposed to an excess of a probe, which also generally functions as a reporter molecule, generally a labeled-antibody or a labeled-antigen reagent (as appropriate), labeled with an enzyme (i.e., an enzyme conjugate), to cause an immunological reaction between the target molecule in the bound sample and the labeled reagent. After removing unreacted labeled reagent or probe from the solid surface, the quantity of bound or unbound labeled reporter molecule is detected or quantified by either contacting the solid surface or the associated liquid phase, respectively, with a detection system containing a signaling reagent, e.g., a substrate for the enzyme that undergoes some detectable change, such as the generation of a colored species, upon reaction with the enzyme.

In a competitive immunoassay, the sample containing an unknown quantity of the target molecule is simultaneously exposed to a solid surface having bound thereto its complementary immunological partner, i.e., bound antigen or bound antibody, with a known amount of a labeled-target molecule. The bound, labeled molecule then is quantitated to determine indirectly the total quantity of target molecule in the sample. At equilibrium, the level of bound labeled target molecule is inversely related to the concentration of the target molecule in the sample.

The reporter molecule (generally either a labeled-antigen or a labeled-antibody) is a heterologous component, usually an enzyme conjugate, which can be detected through a signaling reagent, normally a substrate for the selected enzyme. In the case of an enzyme, a first complex forming site is utilized to attach (usually via a covalent bond) the enzyme to the probe (e.g., to the antigen or antibody, often a polypeptide) and the second (and any additional) complex forming site(s) is(are) utilized to activate the signaling reagent of the detection system, with each complex formed being different and not interfering with each other. The signal thus can be used to demonstrate the presence of the heterologous component and, in turn, the complementary binding partner of the labeled reporter complex (enzyme conjugate).

In a polynucleotide sequence detection assay or polynucleotide hybridization, the non-covalent binding of a labeled polynucleotide sequence or a nucleic acid probe to a complementary sequence of the target molecule is determined under hybridization conditions in accordance with the Watson-Crick base pairing of adenine and thymine, and guanine and cytosine. The nucleic acid probe is modified by a heterologous moiety and the heterologous moiety can be detected through a signaling moiety, in a manner analogous to that described above for immunoassays Techniques also are known for amplifying the signal produced by such assays, indicative of the presence of a target molecule, using for example multiple ligand-receptor pairs. These and other immunoassay and hybridization techniques are well know to those skilled in the art and all can be used in combination with the present invention.

It is an object of this invention, therefore, to provide a novel method of conducting such ligand-receptor assays (e.g., an immunoassay) and polynucleotide hybridizations.

It is another object of this invention to provide a novel detection/signaling system for indicating or quantitating the presence of a target molecule in a sample.

It is a further object of the invention to provide a detection/signaling system for indicating or quantitating the presence of a target molecule in a sample which uses alkaline phosphatase as the reporter enzyme and a reduction of a tetrazolium salt to a formazan as a coloremetric indicator.

It is yet another object of the present invention to provide a storage stable liquid reagent for use as the detection/signaling reagent in an enzyme-linked immunoassay or a polynucleotide hybridization that has an improved sensitivity at low concentrations of the reporter enzyme.

BRIEF DESCRIPTION OF THE DRAWINGS

FIG. 1 illustrates the absorbance as a function of cell concentration for an immunoassay according to the present invention.

DETAILED DESCRIPTION OF THE INVENTION

The present invention is directed to a method for the qualitative detection, or more preferably the quantification, of an unknown amount of a target molecule in a sample, typically immobilized on a solid support, but also more broadly dispersed in a liquid phase. The present invention is specifically directed to an improved enzyme immunoassay (EIA) or an improved polynucleotide hybridization based on a coupled conversion, as described hereinafter, of a tetrazolium salt to a colored formazan dye as the ultimate signaling reagent in the detection system.

The present invention is broadly applicable to all assays based on ligand-receptor interactions, including antigen-antibody interactions and polynucleotide hybridizations. In its preferred form, the invention is directed to an immunoassay or polynucleotide hybridization system in which a heterologous component is attached, either directly or indirectly, to a detector molecule or probe (the detector molecule itself being selectively attached or bound to a target molecule during the assay) and the presence of a detector molecule in a test sample is indicated by an interaction between the heterologous moiety and a redox signaling system.

In particular, the invention uses an alkaline phosphatase conjugate as the heterologous component (reporter molecule or enzyme-label). The enzyme may be attached directly to a detector molecule or probe, which may be the complementary immunological partner of the target molecule or may be a polynucleotide hybrid of the target molecule; or in the broader aspects of the invention, the enzyme may be attached to some intermediate binding partner that is complexed, directly or indirectly, to the detector molecule or probe. For example, in one approach the detector molecule may be a biotin-labeled immunological partner (antibody or antigen) of the target molecule or may be a biotin-labeled polynucleotide hybrid of the target molecule. An alkaline phosphatase-labeled streptavidin complex (alkaline phosphatase conjugate) then could be used as the reporter molecule in the detection system of the present invention. During the immunoassay or hybridization, the alkaline phosphatase conjugate is introduced into an appropriately buffered solution containing any necessary enzyme cofactors and other adjuvants, such as a soluble source of magnesium cations, as well known by those of ordinary skill in the art.

The present invention is specifically based on using the reduction of a tetrazolium salt {e.g., 3-(4,5-dimethyl-2-thiazolyl)-2,5-diphenyl-2H-tetrazolium bromide (thiazolyl blue MTT)} to a formazan (e.g., MTT-formazan) as the way of detecting or quantifying the presence of a target molecule, such as an antigen, an antibody or a polynucleotide, in a sample, particularly a sample of biological origin. In this regard, an alkaline phosphatase conjugate acting as a reporter molecule operates on a substrate {e.g., 5-bromo-4-chloroindoxyl phosphate (BCIP)} to produce an enzymatically altered substrate molecule. The enzymatically altered molecule, in turn, participates with a tetrazolium salt in an oxidation-reduction reaction that causes the formation of a colored formazan species.

A preferred feature of the present invention is the establishment of conditions during the assay to insure the solubilization of the formazan. In this way, the presence of the formazan can be visually identified with the naked eye in qualitative assays or more preferably can be easily quantified by measurement of the absorbance using commercially available colorimetric measurement instrumentation and techniques.

In a preferred embodiment of the invention, the assay typically includes many, but not necessarily all, of the following steps: (i) sample immobilization on a solid phase, (ii) removal of non-immobilized sample, (iii) blocking of the solid phase, as needed, to prevent non-specific binding of the labeled detector molecule or probe, (iv) contacting the sample with the labeled detector molecule or probe to cause an immunological reaction or a polynucleotide hybridization, (v) washing the solid phase, including the sample, to remove excess (including non-specifically bound) labeled detector molecule or probe, and (vi) contacting the sample with a detection system containing a signaling reagent to identify the presence of any labeled detector molecule or probe bound to a target material in the sample.

The terms "bound", "complexed", "attached" and words of similar import are intended throughout the specification and claims to include both covalent and non-covalent interactions, which may be direct or indirect, between two moieties or molecules. An indirect bond or interaction is one where one moiety is attached to another moiety through an intermediate moiety. Methods for forming a labeled detector molecule or probe, for example an antibody having alkaline phosphatase bound thereto are well-known to those skilled in the art and thus require no exposition. Usually, the alkaline phosphatase is covalently bonded to the detector molecule or to an intermediate binding partner that can be complexed, directly or indirectly, to the detector molecule, by direct condensation or by using a known bridging molecule, such as a carbodiimide, a diisocyanate, a dialdehyde or the like.

The term "target material" refers to a material, such as a protein or other molecule, whose presence in a sample is to be detected, identified or quantified. In this regard, typical samples include blood, urine, other bodily fluids, and extracts of other samples.

In accordance with a more specific aspect of the present invention, 5-bromo-4-chloroindoxyl phosphate (BCIP) is used in the detection system as the alkaline phosphatase substrate. BCIP is converted by alkaline phosphatase to the enol 5-bromo-4-chloroindoxyl which, in turn, tautomerizes under alkaline pH conditions to its keto form according to the following reactions:

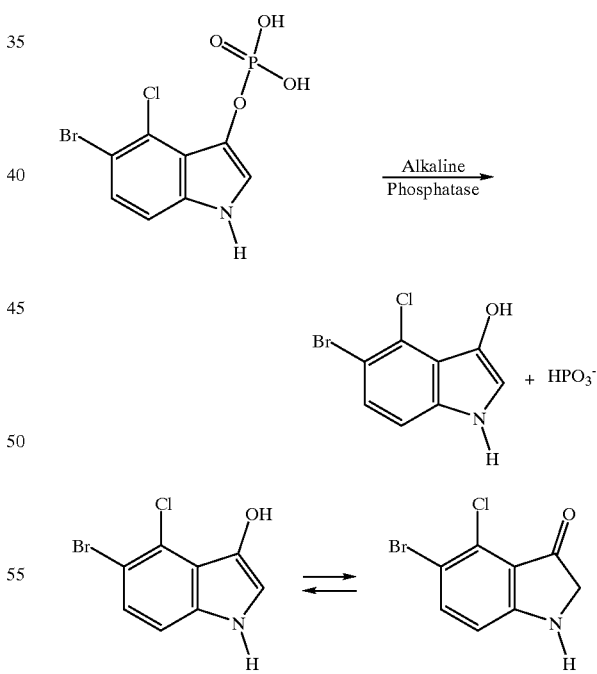

In accordance with the present invention, the keto species thereafter is trapped upon its conversion, by an oxidation to 5,5'-dibromo-4,4'-dichloro-indigo white through a oxidation/reduction (redox) reaction with 3-(4,5-dimethyl-2-thiazolyl)-2,5-diphenyl-2H-tetrazolium bromide (thiazolyl blue MTT) according to the following reaction:

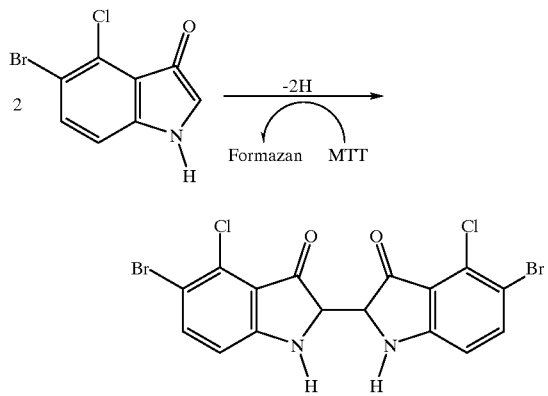

In the redox reaction MTT is reduced to MTT-formazan having a blue color. By allowing this reaction to proceed in an aqueous phase in the presence of an MTT-formazan solubilizing amount of a surfactant, the normally water-insoluble MTT-formazan is made water soluble and can be spectrophotometrically measured using commercially available equipment. Both non-ionic and anionic surfactants generally can be used to enhance the water solubility of the MTT-formazan. Suitable nonionic surfactants include the alkylene oxide adducts of fatty acids, fatty alcohols, tall oil and vegetable oils. For example, polyoxyethylene (23) lauryl ether should be suitable. Other examples include TRITON X-100 and BRIJ non-ionic surfactants. Polymers such as polyvinyl alcohol and polyvinylpryrrolidone also may be used to solubilize the MTT-formazan. Anionic surfactants such as alkyl sulfates and alkyl thioglucosides also can be used. The surfactant generally is included in an amount of 2 to 20 times the weight of the tetrazolium salt. For example sodium lauryl sulfate can be used in an amount of 10 times the weight of the tetrazolium salt. A suitable amount of surfactant to solubilize the MTT-formazan is easily determined by one of ordinary skill in the art using routine testing.

By allowing the detection/signaling reaction(s) to proceed in the aqueous phase, one can determine the increase in concentration of the colored MTT-formazan as a function of time by spectrophotometrically analyzing the aqueous phase. Another important aspect of the present invention involves including certain divalent cations in the solution to enhance the sensitivity of the assay. In particular, such divalent cations are included in the solution in a MTT-formazan sensitivity-enhancing amount. It has been determined that in the presence of such metal cations, the absorbance peak of the MTT-formazan shifts about 50 nm towards the blue end of the visible spectra, but more importantly, the extinction coefficient is enhanced by about 40%. The divalent cation preferably is included in the detection system in a sensitivity enhancing amount of about 20% to 200% by weight of the tetrazolium salt. As a result, commercially available colorimetric detection instrumentation, such as a Biotek Ceres 900 reader, can be used to detect the MTT-formazan chromophore with the required level of sensitivity. Divalent zinc has been found to be a most suitable metal cation in this regard, although other divalent cations such as cadmium and copper can be used, generally with less satisfactory results. Theses cations are suitably introduced into the assay as one of their commonly available water soluble salts; such as zinc chloride, zinc sulfate, zinc acetate, zinc bromide, zinc iodide, zinc propionate, zinc formate, zinc lactate, zinc nitrate, zinc citrate and the like.

Because such cations, in even very small concentrations, i.e., in even micromolar amounts, may inhibit the enzymatic activity of alkaline phosphatase, however, their presence creates a potential problem for optimum use of the assay. The present invention solves this problem by also including a small, but generally critical amount of a relatively weak chelation agent in the assay solution. The chelation agent typically is supplied in the signaling reagent in an amount to provide a mole ratio of said chelation agent to the divalent cation of between about 2 and 100. The strength of the chelation agent must be such that at its concentration in the assay solution the divalent metal cation chelate that is formed in the presence of the alkaline phosphatase dissociates in the presence of the MTT-formazan as it is formed. In connection with the present invention, suitable chelation agents include such weak acids as glycyl glycine, glycine, lactic acid, citric acid and the like, and their derivatives such as their salts and esters. Other weak chelation agents suitable for use in the present invention can be identified by those of ordinary skill in the art using routine testing.

Under one preferred aspect of the present invention, the novel detection method is applied by immobilizing a target molecule, such as an antigen, an antibody or a polynucleotide from a biological sample, on a variety of solid phase supports. Such supports include such materials as hydrocarbon polymers such as a polyolefins, including polystyrene, polyethylene, polypropylene and the like; polyesters; polyamides; cellulose and cellulose derivatives such as nitrocellulose; vinyl polymers such as vinyl chloride, polyvinyl fluoride, polyvinylidene fluoride (PVDF) and the like; nylon; polyacrylic polymers; ion exchange resins and other materials known in the art such as glass. The solid support itself can take many forms including, without limitation, beads, filter paper, test tubes and microtiter plates. A particularly useful form for the solid support is a microtiter well/plate made from polystyrene. The support can be provided with the immunological partners of the target molecule bound to its surface or the surface can be appropriately modified, as needed, before or during the assay to permit binding of the target molecule.

Following immobilization of the target molecule in this preferred embodiment, the solid phase is washed to remove any unbound material and then, in the simplest embodiment, the solid phase is contacted with a reporter molecule complex, i.e., an alkaline phosphatase-labeled complementary immunological partner (i.e., a labeled antigen or a labeled antibody) of the target molecule or an alkaline phosphatase-labeled polynucleotide hybrid of the target molecule, in the presence of any necessary or desired adjuvants as well known to those skilled in the art. The duration of this and any other immunological reaction or polynucleotide hybridization steps in the assay should be sufficient for completion of the accompanying reaction. Suitable times and conditions will be well-recognized by those skilled in this art. A suitable time in many cases will be on the order of 5 minutes or less to 2 hours or more. Gentle agitation of the reagents during such steps may be beneficial.

Upon completion of the immunological or hybridization reaction(s), the support is again washed with an appropriate buffer solution to remove unreacted reagents, such as any unbound labeled detector or reporter molecule complex from the solid support. Such unreacted reagents could interfere with the subsequent detection or quantification step. One suitable wash solution is a phosphate buffered saline solution. Another suitable standard wash solution is an aqueous solution buffered with imidazole to a pH of about 7.0, containing a surfactant in an amount of about 0.02%, such as TWEEN® 20, sodium chloride in an amount of about 0.16M, and ethylene diaminetetraacetic acid (EDTA) in an amount of about 0.5 mM. Those skilled in the art recognize the wide variety of surfactants and buffers that can be used to prepare such standard wash solutions.

At the end of the immunological/hybridization reaction(s) associated with the assay, the enzymatic activity of either the solid or the associated liquid phase, or both, can be determined using the signaling system of the present invention. Assays using the method of the present invention can be run either as endpoint assays or in the format of a kinetic assay. Procedures applicable to either format are well-understood by those skilled in the immunoassay and hybridization art. Reaction(s) between enzyme bound to the solid phase or in the associated liquid phase, or both, and the substrate for the enzyme causes the generation of a colored species through the redox detection/signaling system described above, which is preferably solubilized as described and thus is easily determined or quantified using commercially available spectrophotometric measuring equipment.

As noted above, the alkaline phosphatase enzyme-labeled conjugate preferably is contacted with the signaling reagent containing BCIP, MTT, a MTT-formazan solubilizing amount of a surfactant, a MTT-formazan sensitivity-enhancing amount of a divalent metal cation and a weak chelating agent for said divalent metal cation. After an appropriate period for the various reactions, which may be for example from about 5 minutes to 2 hours, the strength of the colored reaction product is measured. Detection, and preferably quantification, of the sample may be accomplished using any available instrument for assessing the strength of the chromogenic signal. Such analysis might be completed in several seconds and the results can be compared to the strength from a known reference sample as a way of quantifying the concentration of target molecule in the sample. Other ways of quantifying the results will be recognized by those skilled in the art.

For conducting the method of the present invention, a test pack or kit of reagents is generally provided. A kit for conducting an immunoassay in accordance with the present invention, in its simplest form, typically contains one or more of the following components: (1) a quantity of one member of a pair of a ligand-receptor (e.g., antibody-antigen) complementary binding partner bound to a solid phase support; (2) a detector molecule bound to alkaline phosphatase, the detector molecule possibly being one member of the pair of ligand-receptor (e.g., antibody-antigen) complementary binding partners or a polynucleotide hybrid for the target molecule (enzyme conjugate); (3) a signaling system comprising a substrate for the alkaline phosphatase, e.g., BCIP, and a tetrazolium salt, e.g., MTT, in an aqueous solution containing a surfactant, a divalent metal cation and a weak chelating agent. and possibly (4) an immunological binding partner of components (1) or (2). Preferably, to maximize stability during storage of the detection/signaling reagent, MTT is supplied as a separate aqueous solution for mixing with the other components just prior to use.

Reagents used in connection with the present invention also can take many forms. For example, the detector molecule reagent (e.g., a labeled antigen, a labeled antibody or a labeled polynucleotide) can be provided dissolved in an aqueous buffer solution, bound or impregnated on a solid support, such as a paper strip, or as a lyophilized powder. Similarly, while it is preferred to supply the signaling reagent(s) as an aqueous solution, such reagent(s) also could be supplied as a lyophilized powder for reconstitution with water just prior to use.

Although not wishing to be bound to any particular technical explanation, the success of the invention is apparently due to formation of a strongly colored soluble metal MTT-formazan complex under the conditions of the invention as MTT is being reduced by the coupled redox reaction. Prior to the reduction of the MTT, the divalent metal ion exists in a chelated state to prevent enzyme inhibition, The dissociation of the metal chelate complex occurs at a rate similar to the rate of the hydrolysis of the phosphate ester by the alkaline phosphatase. If the rate is too slow, the blue chromophore may not form in concert with the activity of the reporter enzyme. Thus, appropriate organic chelator/metal ion ratios should be selected to maintain the proper balance. If free metal ions exist, enzyme inhibition may occur and conversion of substrate may be diminished.

The following examples are provided for exemplification purposes only and are not intended to limit the scope of the invention which has been described in broad terms above.

EXAMPLE 1

This example describes a suitable composition for a signaling reagent useful in practicing an enzyme immunoassay method of the present invention. The signaling reagent is provided as two separate solutions. Solution A (detailed below) contains the substrate and cofactor for the alkaline phosphatase enzyme, as well as the surfactant, the divalent cations and the weak chelation agent; while solution B (also detailed below) contains the tetrazolium salt. To prepare the ultimate detection/signaling reagent, equal parts of solutions A and B are mixed shortly before use. The mixed solution then is added in an amount of about 100 µl/well to the microtiter plate, which has previously been contacted with a sample and with the alkaline phosphatase-labeled detector. The composition is incubated for about 15 minutes and then each well is read with an ELISA plate reader at 620 nm.

| Solution A | | | Solution B | |
|---|---|---|---|---|
| Tris HCl (pH 9.8) | 100 | mM | MTT | 100 µg/ml |
| NaCitrate | 10 | mM | Water | Balance |
| Sodium lauryl sulfate | 0.1% | | | |
| $MgCl_2$ | 5 | mM | | |
| $ZnCl_2$ | 0.5 | mM | | |
| BCIP | 0.5 | mg/ml | | |
| Water | Balance | | | |

EXAMPLE 2

A quantitative immunoassay was prepared using a specific BCIP/MTT substrate as the signaling reagent. Listeria monocytogenes cells ($2\times10^7$) in 0.10M $NaCO_3$ buffer, 100 µl/well, were added to a 96 well microtiter plate (Nunc), serially diluted in the same buffer and allowed to bind for one hour. Excess antigen was removed and the plate was blocked with 0.2% nonfat dry milk. A specific polyclonal goat antibody (100 µl/well) against Listerial flagellar antigen diluted in 0.1% nonfat milk to 0.5 µg/ml was added to the plate and incubated for 1 hr. The plate was washed with 0.1% TWEEN® 20-PBS buffer. The plate was incubated with 100µl/well with alkaline phosphatase-labeled rabbit anti-goat conjugate IgG(H&L), (0.25 µg/ml in 0.1% nonfat dry milk) for 30 min. The plate was washed as above and 100 µl/well of BCIP/MTT substrate of the composition of Example 1 was added. The plate was incubated for 25 min. And the absorbance of 620 nm was read on a Biotek Ceres 900 plate reader. Values were corrected for background and plotted as a function of relative cell concentration. (See FIG. 1).

EXAMPLE 3

A polynucleotide hybridization assay using the present invention can be conducted as follows. A bacterial cell (pathogen) containing the target polynucleotide sequence is lysed by treatment with an enzyme, solvent or detergent. Single-stranded ribosomal RNA from the bacteria is immobilized on the surface of a microwell plate. The surface then is blocked with bovine serum albumin (BSA) or milk diluent. The immobilized RNA then is incubated with a pathogen specific hapten-labeled DNA or RNA probe (e.g., a biotin-labeled probe) and washed to remove non-hybridized probe. Thereafter, the microwell is contacted with a labeled reporter molecule, e.g., an antibody-labeled or streptavidin-labeled reporter molecule. Following that, the signaling reagent, (BCIP/MTT) is added and incubated for about 20 minutes before the sample is read at 620 nm.

EXAMPLE 4

Another polynucleotide hybridization assay using the present invention can be conducted as follows. A bacterial cell (pathogen) containing the target polynucleotide sequence is lysed by treatment with an enzyme, solvent or detergent. A specific polynucleotide sequence is PCR amplified and is incubated with a pathogen specific hapten-labeled polynucleotide (e.g., a biotin-labeled probe). The hybridized, amplified nucleotides are immobilized (captured) on a microwell plate. Following a method similar to that reported above in Example 3, colorometric detection is conducted using an alkaline phosphatase-labeled streptavidin and the signaling reagent, (BCIP/MTT). The sample is again read at 620 nm.

The principles, preferred embodiments and modes of operation of the present invention have been described in the foregoing specification. While the invention has been exemplified in the specification by reference to particular applications and in the context of specific immunoassay techniques, such as the analysis of blood serum or plasma for the presence of a specific target molecule using a classical sandwich assay, this is done for ease of discussion and presentation and is not intended to be a limit on the broad application of the invention.

Indeed, as will be recognized by those skilled in the art, the present invention can be successfully and usefully adapted to a wide range of immunoassay and hybridization applications such as determining the presence of a protein hormone or its respective antibody complement in a sample, such as in urine or in saliva; determining the presence of a viral or bacterial antigen or their respective antibody complements in a sample, such as in urine or saliva or in an extract or solution of a pharmaceutical product or a food source, and determining the presence of a hapten, such as a vitamin or a steroidal hormone in such samples to name a few, and is similarly useful in the wide variety of immunoassay procedures. In this later regard, one may refer to U.S. Pat. Nos. 3,654,090; 3,819,837; 3,839,153; 4,016,043; 4,020,151; 4,067,959; and 4,376,110 as a few, non-limiting examples of possible immunoassay techniques, both direct and indirect, useful in conjunction with the present invention, the disclosures of which are incorporated herein by reference.

Thus, the invention which is intended to be protected herein is not to be construed as limited to the particular forms disclosed, since they are to be regarded as illustrative rather than restrictive. Variations and changes may be made by those skilled in the art without departing from the spirit of the invention.

We claim:

1. In a method of a polynucleotide hybridization wherein presence in a sample of a target polynucleotide molecule is determined by a detection system comprising a polynucleotide probe which hybridizes to said target and a reporter molecule comprising an enzyme conjugate, and an interaction between said reporter molecule and a signaling reagent signifies the presence of said target molecule in said sample, the improvement comprising:

using alkaline phosphatase in said enzyme conjugate and a combination of 5-bromo-4-chloroindoxyl phosphate (BCIP) and 3-(4,5-dimethyl-2-thiazolyl)-2,5-diphenyl-2H-tetrazolium salt (MTT) as said signaling reagent in said detection system and conducting said interaction in an aqueous phase in the presence of (i) a MTT-formazan solubilizing amount of a surfactant, (ii) a MTT-formazan sensitivity-enhancing amount of a divalent metal cation and (iii) a weak chelating agent for said divalent metal cation, said MTT-formazan sensitivity-enhancing amount of said divalent metal cation being sufficient in the presence of said weak chelating agent to shift MTT-formazan absorbance towards the blue end of the visible spectra and to enhance by about 40% MTT-formazan extinction coefficient, whereby enzymatic conversion of said BCIP is coupled with a conversion of said MTT to MTT-formazan.

2. The method of claim 1 wherein the surfactant is selected from a nonionic polyoxyalkylene surfactant and an anionic surfactant.

3. The method of claim 2 wherein the divalent metal cation originates from a water soluble salt of said divalent metal cation.

4. The method of claim 3 wherein the divalent metal cation is selected from $Zn^{+2}$, $Cd^{+2}$, $Cu^{+2}$ and mixtures thereof.

5. The method of claim 4 wherein said hybridization is conducted in the presence of the divalent metal cation at a concentration of 20% to 200% by weight of the tetrazolium salt.

6. The method of claim 4 wherein the weak chelating agent is selected from the group consisting of glycyl glycine, glycine, lactic acid, citric acid, and salts and esters of glycyl glycine, glycine, lactic acid, citric acid.

7. The method of claim 6 wherein said hybridization is conducted in the presence of 2 to 100 moles of said weak chelating agent to said divalent cation.

8. The method of claim 7 wherein the target molecule is immobilized on a solid phase during said hybridization.

9. The method of claim 8 wherein the solid phase is selected from the group consisting of polystyrene, polyethylene, polypropylene, polyesters, polyamides, cellulose, nitrocellulose, vinyl chloride, polyvinyl fluoride, polyvinylidene fluoride (PVDF), nylon, polyacrylic polymers, ion exchange resins, and glass.

10. The method of claim 2 wherein said hybridization is conducted in the presence of the divalent metal cation at a concentration of 20% to 200% by weight of the tetrazolium salt.

11. The method of claim 10 wherein said hybridization is conducted in the presence of 2 to 100 moles of said weak chelating agent to said divalent cation.

12. The method of claim 1 wherein the divalent metal cation is selected from $Zn^{+2}$, $Cd^{+2}$, $Cu^{+2}$ and mixtures thereof.

13. The method of claim 1 wherein the target molecule is immobilized on a solid phase during said hybridization.

14. In a method of an immunoassay wherein presence in a sample of a target molecule forming one of an antigen-antibody complementary pair is determined by a detection system comprising one of an antigen-antibody complementary pair for binding to said target, a reporter molecule comprising an enzyme conjugate, and an interaction between said reporter molecule and a signaling reagent signifies the presence of said target molecule in said sample, the improvement comprising:

using alkaline phosphatase in said enzyme conjugate and a combination of 5-bromo-4-chloroindoxyl phosphate (BCIP) and 3-(4,5-dimethyl-2-thiazolyl)-2,5-diphenyl-2H-tetrazolium salt (MTT) as said signaling reagent in said detection system and conducting said interaction in an aqueous phase in the presence of (i) a MTT-formazan solubilizing amount of a surfactant, (ii) a MTT-formazan sensitivity-enhancing amount of a divalent metal cation and (iii) a weak chelating agent for said divalent metal cation, said MTT-formazan sensitivity-enhancing amount of said divalent metal cation being sufficient in the presence of said weak chelating agent to shift MTT-formazan absorbance towards the blue end of the visible spectra and to enhance by about 40% MTT-formazan extinction coefficient, whereby enzymatic conversion of said BCIP is coupled with a conversion of said MTT to MTT-formazan.

15. The method of claim 14 wherein the surfactant is selected from a nonionic polyoxyalkylene surfactant and an anionic surfactant.

16. The method of claim 15 wherein the divalent metal cation originates from a water soluble salt of said divalent metal cation.

17. The method of claim 16 wherein the divalent metal cation is selected from $Zn^{+2}$, $Cd^{+2}$, $Cu^{+2}$ and mixtures thereof.

18. The method of claim 17 wherein said immunoassay is conducted in the presence of the divalent metal cation at a concentration of 20% to 200% by weight of the tetrazolium salt.

19. The method of claim 17 wherein the weak chelating agent is selected from the group consisting of glycyl glycine, glycine, lactic acid, citric acid, and salts and esters of glycyl glycine, glycine, lactic acid, citric acid.

20. The method of claim 19 wherein said immunoassay is conducted in the presence of 2 to 100 moles of said weak chelating agent to said divalent cation.

21. The method of claim 20 wherein the target molecule is immobilized on a solid phase during said immunoassay.

22. The method of claim 21 wherein the solid phase is selected from the group consisting of polystyrene, polyethylene, polypropylene, polyesters, polyamides, cellulose, nitrocellulose, vinyl chloride, polyvinyl fluoride, polyvinylidene fluoride (PVDF), nylon, polyacrylic polymers, ion exchange resins, and glass.

23. The method of claim 15 wherein said immunoassay is conducted in the presence of the divalent metal cation at a concentration of 20% to 200% by weight of the tetrazolium salt.

24. The method of claim 23 wherein said immunoassay is conducted in the presence of 2 to 100 moles of said weak chelating agent to said divalent cation.

25. The method of claim 14 wherein the divalent metal cation is selected from $Zn^{+2}$, $Cd^{+2}$, $Cu^{+2}$ and mixtures thereof.

26. The method of claim 14 wherein the target molecule is immobilized on a solid phase during said immunoassay.

27. An immunoassay kit for determining the presence in a sample of a target molecule forming one of an antigen-antibody complementary pair using a detection system comprising one of an antigen-antibody complementary pair for binding to said target, a reporter molecule comprising an enzyme conjugate, and a signaling reagent to signify the presence of said target molecule in said sample, said kit comprising an alkaline phosphatase conjugate as said reporter molecule, a first aqueous solution comprising 5-bromo-4-chloroindoxyl phosphate (BCIP), a surfactant, a weak chelating agent, and a divalent cation in a MTT-formazan sensitivity-enhancing amount sufficient in the presence of said weak chelating agent to shift MTT-formazan absorbance towards the blue end of the visible spectra and to enhance by about 40% MTT-formazan extinction coefficient and a second aqueous solution of 3-(4,5-dimethyl-2-thiazolyl)-2,5-diphenyl-2H-tetrazolium salt (MTT) as said signaling reagent, and a sample well comprising a solid phase for immobilizing said target molecule during said immunoassay.

28. A polynucleotide hybridization kit for determining the presence in a sample of a target polynucleotide molecule using a detection system comprising a polynucleotide probe which hybridizes to said target, a reporter molecule comprising an enzyme conjugate, and a signaling reagent to signify the presence of said target molecule in said sample, said kit comprising an alkaline phosphatase conjugate as said reporter molecule, a first aqueous solution comprising 5-bromo-4-chloroindoxyl phosphate (BCIP), a surfactant, a weak chelating agent, and a divalent cation in a MTT-formazan sensitivity-enhancing amount sufficient in the presence of said weak chelating agent to shift MTT-formazan absorbance towards the blue end of the visible spectra and to enhance by about 40% MTT-formazan extinction coefficient and a second aqueous solution of 3-(4,5-dimethyl-2-thiazolyl)-2,5-diphenyl-2H-tetrazolium salt (MTT) as said signaling reagent, and a sample well comprising a solid phase for immobilizing said target molecule during said hybridization.

* * * * *